(12) United States Patent
Bottom et al.

(10) Patent No.: US 11,045,617 B2
(45) Date of Patent: Jun. 29, 2021

(54) INTUBATION AIDS

(71) Applicant: INTERSURGICAL AG, Vaduz (LI)

(72) Inventors: David Simon Bottom, Wokingham (GB); Andrew Neil Miller, Wokingham (GB); Richard Mark Levitan, Orford, NH (US)

(73) Assignee: INTERSURGICAL AG, Vaduz (LI)

( * ) Notice: Subject to any disclaimer, the term of this patent is extended or adjusted under 35 U.S.C. 154(b) by 132 days.

(21) Appl. No.: 16/075,226

(22) PCT Filed: Feb. 3, 2017

(86) PCT No.: PCT/EP2017/052474
§ 371 (c)(1),
(2) Date: Aug. 3, 2018

(87) PCT Pub. No.: WO2017/134284
PCT Pub. Date: Aug. 10, 2017

(65) Prior Publication Data
US 2019/0038861 A1    Feb. 7, 2019

(30) Foreign Application Priority Data
Feb. 4, 2016  (GB) ...................................... 1602049

(51) Int. Cl.
*A61M 16/04* (2006.01)
*A61M 25/01* (2006.01)

(52) U.S. Cl.
CPC ........ *A61M 16/0429* (2014.02); *A61M 16/04* (2013.01); *A61M 16/0431* (2014.02); *A61M 16/0488* (2013.01); *A61M 25/0102* (2013.01)

(58) Field of Classification Search
CPC .......... A61M 16/0429; A61M 16/0431; A61M 16/04; A61M 25/0102; A61M 16/0488; A61M 25/102; A61M 25/01; A61M 25/0152; A61M 25/0063; A61B 1/267
See application file for complete search history.

(56) References Cited

U.S. PATENT DOCUMENTS

| 3,957,055 A | 5/1976 | Linder et al. |
| 4,448,741 A | 5/1984 | Schad |
| 5,259,377 A | 11/1993 | Schroeder |

(Continued)

FOREIGN PATENT DOCUMENTS

| EP | 0465942 A1 | 1/1992 |
| EP | 1786362 B1 | 4/2015 |

(Continued)

OTHER PUBLICATIONS

Great Britain Search Report for corresponding GB1602049.7 (dated Dec. 9, 2016).

(Continued)

*Primary Examiner* — Joseph D. Boecker
*Assistant Examiner* — Thomas W Greig
(74) *Attorney, Agent, or Firm* — Mendelsohn Dunleavy, P.C.; Steve Mendelsohn

(57) ABSTRACT

An intubation aid (10) for insertion into an endotracheal tube (30) has a cross-sectional shape having at least one vertex defining a longitudinally extending edge. The intubation aid (10) is supported within the endotracheal tube (30), in use, by the longitudinally extending edge.

18 Claims, 6 Drawing Sheets

(56) References Cited

U.S. PATENT DOCUMENTS

| | | |
|---|---|---|
| 5,529,738 A | 6/1996 | Mercereau |
| 5,761,759 A | 6/1998 | Leversby et al. |
| 5,769,506 A | 6/1998 | Boucherie |
| 6,579,485 B2 | 6/2003 | Smith et al. |
| 6,972,106 B2 | 12/2005 | Huber et al. |
| 7,083,756 B2 | 8/2006 | Strahler |
| 7,108,815 B2 | 9/2006 | Lee |
| 7,650,886 B1 | 1/2010 | Keller et al. |
| 7,655,543 B2 | 2/2010 | Bauer |
| 8,066,926 B2 | 11/2011 | Fogarty |
| 8,435,433 B2 | 5/2013 | Pennell et al. |
| 9,844,899 B2 | 12/2017 | Gauthier et al. |
| 10,105,886 B2 | 10/2018 | Maslakow et al. |
| 10,569,039 B2 * | 2/2020 | Levitan ............ A61M 16/0488 |
| 2002/0074688 A1 | 6/2002 | Smith et al. |
| 2002/0171169 A1 | 11/2002 | Chuang |
| 2005/0244611 A1 | 11/2005 | Deininger et al. |
| 2006/0110704 A1 | 5/2006 | Bills |
| 2007/0287961 A1 | 12/2007 | Parker |
| 2007/0290399 A1 | 12/2007 | Easter et al. |
| 2008/0017195 A1 | 1/2008 | Yoshida |
| 2008/0087795 A1 | 4/2008 | Smith |
| 2009/0161063 A1 | 6/2009 | Parent |
| 2010/0108060 A1 | 5/2010 | Pecherer et al. |
| 2010/0152678 A1 | 6/2010 | Jakob |
| 2011/0120458 A1 | 5/2011 | Schwartz et al. |
| 2011/0265789 A1 | 11/2011 | Gabriel |
| 2012/0204867 A1 * | 8/2012 | Levitan ............ A61B 17/3209 128/200.26 |
| 2012/0298102 A1 * | 11/2012 | Levitan ............ A61M 16/0472 128/200.26 |
| 2013/0035548 A1 | 2/2013 | Ianchulev |
| 2013/0096482 A1 * | 4/2013 | Bertrand .......... A61M 25/0102 604/8 |
| 2013/0211263 A1 * | 8/2013 | Boedeker .......... A61M 16/0488 600/478 |
| 2013/0245372 A1 | 9/2013 | Lo |
| 2014/0165799 A1 | 6/2014 | Gauthier et al. |
| 2014/0238390 A1 | 8/2014 | Wei et al. |
| 2015/0080989 A1 | 3/2015 | Mohn et al. |
| 2015/0042011 A1 | 4/2015 | Huang |
| 2015/0290414 A1 * | 10/2015 | Vasan ............... A61M 16/0488 600/191 |

FOREIGN PATENT DOCUMENTS

| | | |
|---|---|---|
| GB | 2017504 B | 9/1982 |
| GB | 2507474 A | 5/2014 |
| JP | H01174426 A | 7/1989 |
| JP | H06170889 A | 6/1994 |
| WO | 93/10840 A1 | 6/1993 |
| WO | 2006/017667 A1 | 2/2006 |
| WO | 2007/093786 A1 | 8/2007 |
| WO | 2013/059324 A1 | 4/2013 |
| WO | 2015/157657 A1 | 10/2015 |

OTHER PUBLICATIONS

PCT International Search Report and Written Opinion for corresponding PCT/EP2017/052474 (dated Apr. 10, 2017).
International Preliminary Report on Patentability for International Patent Application Serial No. PCT/EP2017/052474, 6 pages (dated Aug. 7, 2018).
EUIPO Design Registration No. 002600932-0001; Registered on Dec. 18, 2014; Owner: VBM Medizintechnik GmbH (4 pages).
First Office Action for corresponding Chinese application No. 201680064845.4; dated Sep. 25, 2019; Machine Translation (15 pages).
First Office Action for corresponding Chinese application No. 201780009914.6; dated Jul. 3, 2020; Machine Translation (20 pages).
Second Office Action for Chinese application No. 201680064845.4; dated Jun. 30, 2020; 16 pages (Machine Translation).
Communication pursuant to Article 94(3) EPC for European application No. 16797483.1; dated Jun. 3, 2020; (4 pages).
Non-Final Office Action for U.S. Appl. No. 15/773,923; dated Aug. 20, 2020 (10 pages).
Final Office Action for U.S. Appl. No. 15/773,923; dated Mar. 1, 2021 (10 pages).

* cited by examiner

INTUBATION AIDS

This application is a national stage application under 35 U.S.C. § 371 of PCT International Application Serial No. PCT/EP2017/052474, filed Feb. 3, 2017, which claims priority benefit of Great Britain Application No. 1602049.7, filed Feb. 4, 2016, each of which is hereby incorporated by reference in its entirety.

The present invention relates to intubation aids, and more particularly to bougies or stylets for use in intubation.

Endotracheal tubes are tubes that are inserted into the trachea of a patient in order to establish a patient airway, thereby ensuring the adequate exchange of oxygen and carbon dioxide. The process of introducing an endotracheal tube into the trachea is called tracheal intubation, or simply intubation. Intubation aids are used to ensure the correct positioning of an endotracheal tube within the trachea of a patient, and bougies and stylets are common examples of intubation aids.

Bougies are flexible devices that are used to provide a positive position within the trachea for guiding an endotracheal tube into the trachea. Although bougies are flexible, these devices are typically formable to at least some degree, and typically include an obliquely angled tip, which may assist placement of a distal end of the bougie within the trachea. It is common to introduce a bougie into the trachea using a laryngoscope, ie during a laryngoscopy, such that a distal end of the bougie is located within the trachea, and a proximal end of the bougie projects from the patient's mouth. Once the distal end of the bougie is placed in the trachea, the laryngoscope is removed. An endotracheal tube is then "railroaded" over the bougie, which involves inserting the proximal end of the bougie into a distal end of the endotracheal tube, and sliding the endotracheal tube over, and along, the external surface of the bougie until the distal end of the endotracheal tube is appropriately positioned within the trachea. The bougie therefore acts as a guide for placement of the endotracheal tube. The bougie is then removed from the endotracheal tube and the patient.

A common problem with bougies is excessive friction between the bougie and the endotracheal tube, which may cause difficulties when introducing the endotracheal tube or when withdrawing the bougie. This problem is conventionally addressed by the use of a lubricating fluid. However, such lubricating fluid can result in an exterior surface of the bougie becoming slippery, and more difficult to control by a user.

Stylets are malleable devices that are inserted into an endotracheal tube prior to insertion of the endotracheal tube into the trachea of a patient. The malleable nature of the stylet allows a user to pre-form the endotracheal tube to a desired shape prior to insertion into the trachea. It is common to introduce an endotracheal tube into the trachea using a laryngoscope, ie during a laryngoscopy, such that a distal end of the endotracheal tube is located within the trachea, and a proximal end of the endotracheal tube projects from the patient's mouth. Once the distal end of the endotracheal tube is appropriately positioned within the trachea, the stylet is withdrawn and removed, along with the laryngoscope.

A common problem with stylets is excessive friction between the stylet and the endotracheal tube, which may cause difficulties when withdrawing the stylet. This problem is conventionally addressed by the use of a lubricating fluid. However, such lubricating fluid can result in an exterior surface of the stylet becoming slippery, and more difficult to control by a user.

There has now been devised an intubation aid which overcomes or substantially mitigates the aforementioned and/or other disadvantages associated with the prior art.

According to a first aspect of the present invention there is provided an intubation aid for insertion into an endotracheal tube, the intubation aid comprising a cross-sectional shape having at least one vertex defining a longitudinally extending edge, such that the intubation aid is supported within the endotracheal tube, in use, by the longitudinally extending edge.

The intubation aid according to the first aspect of the present invention is beneficial principally as the longitudinally extending edge may reduce friction between the intubation aid and an interior surface of an endotracheal tube, in use, and/or may reduce the resistance to insertion/withdrawal between the intubation aid and an endotracheal tube, in use. In particular, the longitudinally extending edge may reduce a surface area of the intubation aid which is in contact with an interior surface of an endotracheal tube in use.

Furthermore, the longitudinally extending edge may be graspable by a user, in use, and may thus provide a user with increased grip and control when manipulating the intubation aid.

Outer faces of the intubation aid may not contact an internal surface of an endotracheal tube during insertion and/or removal of the intubation aid from the interior of the endotracheal tube. Outer faces of the intubation aid which are adjacent to the longitudinally extending edge may not contact an internal surface of an endotracheal tube during insertion and/or removal of the intubation aid from the interior of the endotracheal tube. Outer faces of the intubation aid may be substantially planar and/or substantially concave in form. Outer faces of the intubation aid may be substantially convex in form only to the extent that the outer faces do not contact an interior surface of an endotracheal tube in use. An endotracheal tube is typically substantially cylindrical in form, and thus typically has a substantially circular cross sectional shape.

By cross-sectional shape is meant the cross-sectional shape visible when a planar cut is taken through the intubation aid, substantially orthogonal to the longitudinal axis of the intubation aid.

By longitudinally extending edge is meant an edge which extends at least partially along the length of the intubation aid, ie parallel to, or substantially parallel to, a central longitudinal axis of the intubation aid.

The intubation aid may comprise a bougie and/or stylet.

The intubation aid may comprise a proximal end and a distal end, and at least a portion of the intubation aid between the proximal end and the distal end may comprise a cross-sectional shape having at least one vertex defining a longitudinally extending edge. The at least a portion of the intubation aid which has a cross-sectional shape having at least one vertex may be referred to as a main body portion. The main body portion may contact an interior surface of an endotracheal tube in use.

The main body portion may comprise at least two regions having different cross-sectional shapes. The main body portion may comprise at least one region comprising a regular polygonal cross-section and at least one region comprising an irregular polygonal cross-section. At least one region of the main body portion may comprise at least one dimension which is altered, for example increased or decreased, relative to corresponding dimensions of the cross-sectional shape of another region of the main body portion, for example an altered height and/or width. The cross-sectional shape of a region of the main body portion may comprise a decreased height relative to the corresponding height of the cross-sectional shape of another region of the main body portion, whilst having the same or a greater width, for example such that the cross-sectional shape of the main body portion appears flattened in some regions of the main body portion compared to others.

At least one region of the main body portion may comprise a cross-sectional shape having orthogonal major and minor axes, for example axes having the longest and shortest widths and/or heights of the cross-sectional shape. The major axis may be at least 1.1 times, at least 1.2 times, at least 1.3 times, at least 1.4 times, at least 1.5 times, at least 2 times, at least 3 times, at least 4 times, or at least 5 times, larger than the minor axis.

At least one vertex of the cross-sectional shape may be located along the major axis. Opposing vertices of the cross-sectional shape may be located along the major axis. At least one vertex of the cross-sectional shape may be located orthogonally relative to the minor axis. Opposing vertices of the cross-sectional; shape may be located orthogonally to the minor axis.

At least one region of the main body portion may comprise at least one face of increased surface area relative to the other faces of that region. The at least one face of increased surface area may intersect the minor axis of a cross-sectional shape of that region, and may, for example, be bisected by the minor axis of a cross-sectional shape of that region. The at least one face of increased surface area may be arranged such that the minor axis of a cross-sectional shape of the region is normal to that face. The at least one face may have a transverse axis in the plane of the face that is substantially parallel to the major axis of a cross-sectional shape of the region, for example whilst being spaced apart from the major axis.

The at least one face of increased surface area may comprise a pair of opposing edges defined by longitudinally extending edges of the intubation aid. The at least one face of increased surface area may extend along a longitudinal axis of the intubation aid.

At least one region of the main body portion may comprise a cross-sectional shape defining a pair of surfaces of increased surface area relative to the other faces defined by the cross-sectional shape. The pair of faces of increased surface area may intersect the minor axis, and may, for example, be bisected by the minor axis. The pair of faces of increased surface area may be substantially orthogonal to the minor axis. The pair of faces may be substantially parallel to the major axis, for example whilst being spaced apart from the major axis. Each of the pair of faces may be equidistantly spaced from the major axis.

A plurality of portions of the intubation aid may comprise a cross-sectional shape having at least one vertex defining a longitudinally extending edge. The plurality of portions may be spaced apart from one another, and may, for example, be spaced apart by portions of the intubation aid comprising a cross-sectional shape having fewer vertices and/or a cross-sectional shape having differing dimensions.

The proximal end and the distal end may comprise respective proximal and distal end regions of the intubation aid. The cross-sectional shape having at least one vertex may be located between the proximal and distal end regions.

The intubation aid may be configured to fit within an endotracheal tube. The intubation aid may be shaped and/or dimensioned to fit within an endotracheal tube. The intubation aid may be substantially elongate in form. The intubation aid may have a diameter, for example an outer diameter, of between 1.0 mm and 10.0 mm. The intubation aid may have a diameter of between 2.0 mm and 5.0 mm. The intubation aid may have a length between 100 mm and 1000 mm. The intubation aid may have a length between 200 mm and 700 mm. Where the intubation aid comprises a stylet, the intubation aid may have a length between 200 mm and 400 mm, and may, for example, have a length between 225 mm and 365 mm. Where the intubation aid comprises a bougie, the intubation aid may have a length of at most 1000 mm, at most 900 mm, at most 800 mm, or at most 700 mm.

The intubation aid may comprise a cross-sectional shape having at least one vertex along substantially the entire length of the intubation aid, such that a longitudinally extending edge is defined along substantially the entire length of the intubation aid. The intubation aid may comprise a cross-sectional shape having at least one vertex between the proximal and distal end regions. The at least one vertex may be rounded.

Where the cross-sectional shape comprises more than one vertex, each vertex may define a different longitudinally extending edge.

The cross-sectional shape may be substantially polygonal. The intubation aid may comprise a substantially polyhedral global form. Vertices of the polygonal cross-section may correspond to edges of the polyhedral global form. Vertices of the polygonal cross-section and/or edges of the polyhedral global form may be rounded. Faces of the polyhedral global form may be substantially planar.

The polygonal cross-section may comprise at least three vertices. The polygonal cross-section may comprise six vertices, and may be substantially hexagonal in form.

The intubation aid may comprise a distal end, and the distal end of the intubation aid may comprise a rounded tip. By distal end is meant an end of the intubation aid which enters the trachea of a patient first during use. The distal end may be configured to fit within an interior of an endotracheal tube. The distal end may be shaped and dimensioned to fit within an interior of an endotracheal tube. The rounded tip may comprise a circular cross-section and/or may comprise a substantially hemi-spherical global form. The rounded tip may be angled relative to the main body portion, and may for example, be obliquely angled relative to the main body portion.

The rounded tip may be beneficial as it may reduce the risk of trauma to a patient's anatomy during use of the intubation aid. The rounded tip may be beneficial as it may provide tactile feedback to a user during insertion of the intubation aid into a trachea of a patient, in use, and may, for example, provide tactile feedback when the rounded tip passes over tracheal rings of a patient, in use. The intubation aid may be dimensioned such that, when inserted into an endotracheal tube, only the rounded tip extends out of a distal end of the endotracheal tube.

The rounded tip may be integrally formed with the intubation aid, and may, for example, be formed as part of an integral moulding process with the remainder of the intubation aid.

The intubation aid may comprise a unitary body, for example a body having no additional and/or removable components. The intubation aid may not comprise electronic components. The intubation aid may be formed as part of a single moulding process, or may be formed as part of a multiple shot moulding process.

The intubation aid may comprise a proximal end. The proximal end may be configured to fit within an interior of an endotracheal tube. The proximal end may be shaped and dimensioned to fit within an interior of an endotracheal tube.

A proximal end region of the intubation aid may comprise a grip, for example a portion of the intubation aid which is graspable by a user during use. The grip may be graspable by a user's digits and/or the palm of a user's hand, in use. The grip may be formed by a bend in the intubation aid and/or at least a partial loop formed by the intubation aid. The grip may comprise a polygonal cross-section, for example a hexagonal cross section. A grip having a polygonal cross-section may be advantageous as such a handle may allow for enhanced user control of the intubation aid in use. In particular, a polygonal cross-section may allow for more accurate rotation of the intubation aid, and/or may prevent a user's grip from slipping on the intubation aid, in use, as the planar surfaces of the polyhedral global form may allow for increased grip by a user, whilst the longitudinally extending edges may prevent a user's grip from slipping in use.

Furthermore, a polygonal cross-section may allow a user to better visualise and/or feel rotation of the intubation aid within an endotracheal tube, thus providing enhanced control over rotation, and an increased control over placement of the proximal tip within the trachea of a patient.

The proximal end region of the intubation aid may comprise a region of reduced size, for example reduced width or diameter. The proximal end region of the intubation aid may comprise a taper. For example, the proximal end region of the intubation aid may reduce gradually in width toward the proximal end of the intubation aid. The proximal end region of the intubation aid may have a cut-out and/or recessed portion corresponding to at least a portion of the polygonal cross-section, such that the proximal end region of the intubation aid is locatable substantially flush with the polygonal cross-section. The cut-out and/or recessed portion may be substantially triangular or trapezoidal in form.

This may allow the proximal end region of the intubation aid to be located in a proximal region of an endotracheal tube, along with the main body of the intubation aid, in use, such that the endotracheal tube is retained in position, and at a certain depth, relative to the intubation aid. For example, the combined width of the main body and the proximal end region may correspond to the internal width of an endotracheal tube, such that the endotracheal tube is held in position by a friction fit. This may also allow the rotational alignment of the intubation aid and/or endotracheal tube and/or distal tip to be retained, in use. Furthermore, cooperation between the cut-out and/or recessed portion, and at least a portion of the polygonal cross-section, may fix the position of the proximal end relative to the main body, for example such that the proximal end cannot rotate relative to the main body. In such a manner, the alignment of the rounded tip may be known to a user by the positioning of the proximal end, in use. This may be particularly beneficial in retaining alignment of the rounded tip relative to a distal end, for example a bevelled end, of an endotracheal tube, in use.

Where the proximal end region of the intubation aid is located in a proximal region of an endotracheal tube, along with the main body of the intubation aid, the intubation aid may form at least a partial loop. The at least a partial loop may comprise a handle, which may be graspable by a user in use. The handle may receive a user's digits and/or at least a portion of a user's palm in use. The handle may comprise a cross-sectional shape having at least one vertex defining a longitudinally extending edge. Thus the handle may provide increased control to a user, in use.

The handle may comprise a different cross-sectional shape to the main body portion. The handle may comprise an irregular polygonal cross-section whilst the main body portion comprises a regular polygonal cross-section. The cross-sectional shape of the handle may comprise at least one dimension which has been altered, for example increased or decreased, relative to corresponding dimensions of the cross-sectional shape of the main body portion, for example an altered height and/or width. The cross-sectional shape of the handle may comprise a decreased height relative to the corresponding height of the cross-sectional shape of the main body portion, for example such that the cross-sectional shape of the handle appears flattened relative to the cross-sectional shape of the main body portion.

The handle may comprise a cross-sectional shape having orthogonal major and minor axes, for example axes having the longest and shortest widths and/or heights of the cross-sectional shape.

At handle may comprise a cross-sectional shape having orthogonal major and minor axis, for example axes having the longest and shortest widths and/or heights of the cross-sectional shape. The major axis may be at least 1.1 times, at least 1.2 times, at least 1.3 times, at least 1.4 times, at least 1.5 times, at least 2 times, at least 3 times, at least 4 times, or at least 5 times, larger than the minor axis.

At least one vertex of the cross-sectional shape may be located along the major axis. Opposing vertices of the cross-sectional shape may be located along the major axis. At least one vertex of the cross-sectional shape may be located orthogonally relative to the minor axis. Opposing vertices of the cross-sectional; shape may be located orthogonally to the minor axis.

The handle may comprise a cross-sectional shape defining at least one face of increased surface area relative to the other faces defined by the cross-sectional shape. The at least one face of increased surface area may intersect the minor axis, and may, for example, be bisected by the minor axis. The at least one face of increased surface area may be substantially orthogonal to the minor axis. The at least one face may be substantially parallel to the major axis, for example whilst being spaced apart from the major axis.

The at least one face of increased surface area may comprise a pair of opposing edges defined by longitudinally extending edges of the intubation aid. The at least one face of increased surface area may extend along a longitudinal axis of the intubation aid.

The handle may comprise a cross-sectional shape defining a pair of surfaces of increased surface area relative to the other faces defined by the cross-sectional shape. The pair of faces of increased surface area may intersect the minor axis, and may, for example, be bisected by the minor axis. The pair of faces of increased surface area may be substantially orthogonal to the minor axis. The pair of faces may be substantially parallel to the major axis, for example whilst being spaced apart from the major axis. Each of the pair of faces may be equidistantly spaced from the major axis.

The handle may comprise a cross-sectional shape defining opposing faces of increased surface area relative to the other faces defined by the cross-sectional shape. The opposing faces of increased surface area may be located as inner and outer faces of the handle where the proximal end region of the intubation aid is located in a proximal region of an endotracheal tube. The minor axis of the cross-sectional shape may be located in a single plane for substantially the entire length of the handle where the proximal end region of the intubation aid is located in a proximal region of an endotracheal tube.

It has been found that a flattened cross-sectional shape of handle relative to the cross-sectional shape of the main body portion may reduce kinking, eg relative movement between different sections of the intubation aid, where the proximal end region of the intubation aid is located in a proximal region of an endotracheal tube, along with at least a portion of the main body of the intubation aid, such that the intubation aid forms at least a partial loop.

The at least one face of increased surface area may be engageable with a face of a proximal end region of the intubation aid where the proximal end region of the intubation aid is located in a proximal region of an endotracheal tube, for example such that the at least one face of increased surface area is substantially flush with a face of a proximal end region of the intubation aid. The at least one face of increased surface area and a face of a proximal end region of the intubation aid may comprise congruent faces where the proximal end region of the intubation aid is located in a proximal region of an endotracheal tube. Thus the increased surface area and reduced height or may increase frictional engagement, and thereby act to retain the proximal end region of the intubation aid in a proximal region of an endotracheal tube.

According to a further aspect of the present invention there is provided an intubation aid for insertion into an endotracheal tube, at least a portion of the intubation aid comprising a cross-sectional shape having major and minor axes.

The cross-sectional shape may or may not comprise vertices.

Where the cross-sectional shape does not comprise any vertices, it may be possible to superimpose a circle over the cross-sectional shape, such that the circle intersects opposing end points of the major axis without intersecting opposing end points of the minor axis. Where the cross-sectional shape does not comprise any vertices, it may be possible to superimpose a circle over the cross-sectional shape, such that opposing end points of the major axis lie on the perimeter of the circle whilst opposing end points of the minor axis lie within the perimeter of the circle.

Where the cross-sectional shape comprises a plurality of vertices, the cross-sectional shape may comprise vertices located at either end of the major axis. Where the cross-sectional shape comprises a plurality of vertices, it may be possible to superimpose a circle over the cross-sectional shape, such that the circle intersects at least two vertices of the cross-sectional shape without intersecting at least one other vertex of the cross-sectional shape. It may be possible to superimpose a circle over the cross-sectional shape such that opposing vertices at end points of the major axis lie on the perimeter of the circle whilst at least one other vertex of the cross-sectional shapes lies within the perimeter of the circle.

A first radial line that is normal to a first straight connecting line intersecting a first pair of adjacent vertices may have a first length between the first connecting line and a centre-point of the cross-sectional shape. A second radial line that is normal to a second straight connecting line intersecting a second pair of adjacent vertices may have a second length between the second connecting line and the centre-point of the cross-sectional shape. The first length may be greater than the second length.

The cross-sectional shape may define a shape having at least two sides, such that the intubation aid comprises at least two longitudinally extending faces. A first radial line that is normal to a first side of the cross-sectional shape may have a first length between the first side and a centre-point of the cross-sectional shape. A second radial line that is normal to a second side of the cross-sectional shape may have a second length between the second side and the centre-point of the cross-sectional shape. The first length may be greater than the second length.

This aspect of the present invention may be advantageous as where the intubation aid is bent to a significant degree this aspect of the present invention may reduce kinking of the device, for example relative lateral movement between at least two regions of the intubation aid.

For example, when a proximal end region of the intubation aid is located in a proximal region of an endotracheal tube, along with the at least a portion of the intubation aid comprising a cross-sectional shape having major and minor axes, kinking of the device, for example relative lateral movement between at least two regions of the intubation aid, may be reduced.

According to a further aspect of the present invention there is provided a method of forming an intubation aid for insertion into an endotracheal tube, at least a portion of the intubation aid comprising a cross-sectional shape having major and minor axes, wherein the method comprises moulding the intubation aid such that at least a portion of the intubation aid comprises a cross-sectional shape having major and minor axes.

The method may comprise moulding the intubation aid such that at least a portion of the intubation aid comprises a cross-sectional shape having major and minor axes, without any intermediate steps.

The proximal end region may comprise a region having a cross-sectional shape corresponding to the shape of an interior surface of an endotracheal tube. The proximal end region may comprise a region having an arcuate cross-sectional shape. The arcuate cross-sectional shape may contact an interior surface of an endotracheal tube when the proximal end region is inserted into an endotracheal tube, in use. This may increase friction when the proximal end region is inserted into an endotracheal tube along with the main body portion, thereby increasing resistance to rotation of the intubation aid relative to the endotracheal tube in such a configuration.

At least a portion of the intubation aid may be flexible. The flexible portion may be formable, at least to some degree. The distal end region and/or the proximal end region may be flexible. At least a portion of the intubation aid may comprise a flexible core. The flexible core may, for example, comprise woven polyester, or solid plastic, or the like.

At least a portion of the intubation aid may be malleable. For example, at least a portion of the intubation aid may be may be adapted substantially to retain its shape once deformed, eg at least against the action of gravity. The degree of malleability may be selected as required, eg for the particular function. The at least one malleable portion may be chosen to be sufficiently flexible to deform, eg lose its retained shape, as the intubation aid is removed from a patient. The main body portion may comprise at least one malleable region. At least a portion of the intubation aid may comprise malleable core. The malleable core may, for example, comprise aluminium or the like.

The intubation aid may comprise an outer surface formed of any suitable plastics material. The intubation aid may comprise, for example, an outer surface formed of polyvinyl chloride (PVC). The intubation aid may comprise an outer surface formed of latex or polyolefin, for example polyethylene.

According to a second aspect of the present invention, there is provided apparatus comprising an endotracheal tube and an intubation aid according to the first aspect of the present invention.

A practicable embodiment of the invention is described in further detail below, with reference to the accompanying drawings, of which:

Figure 1:
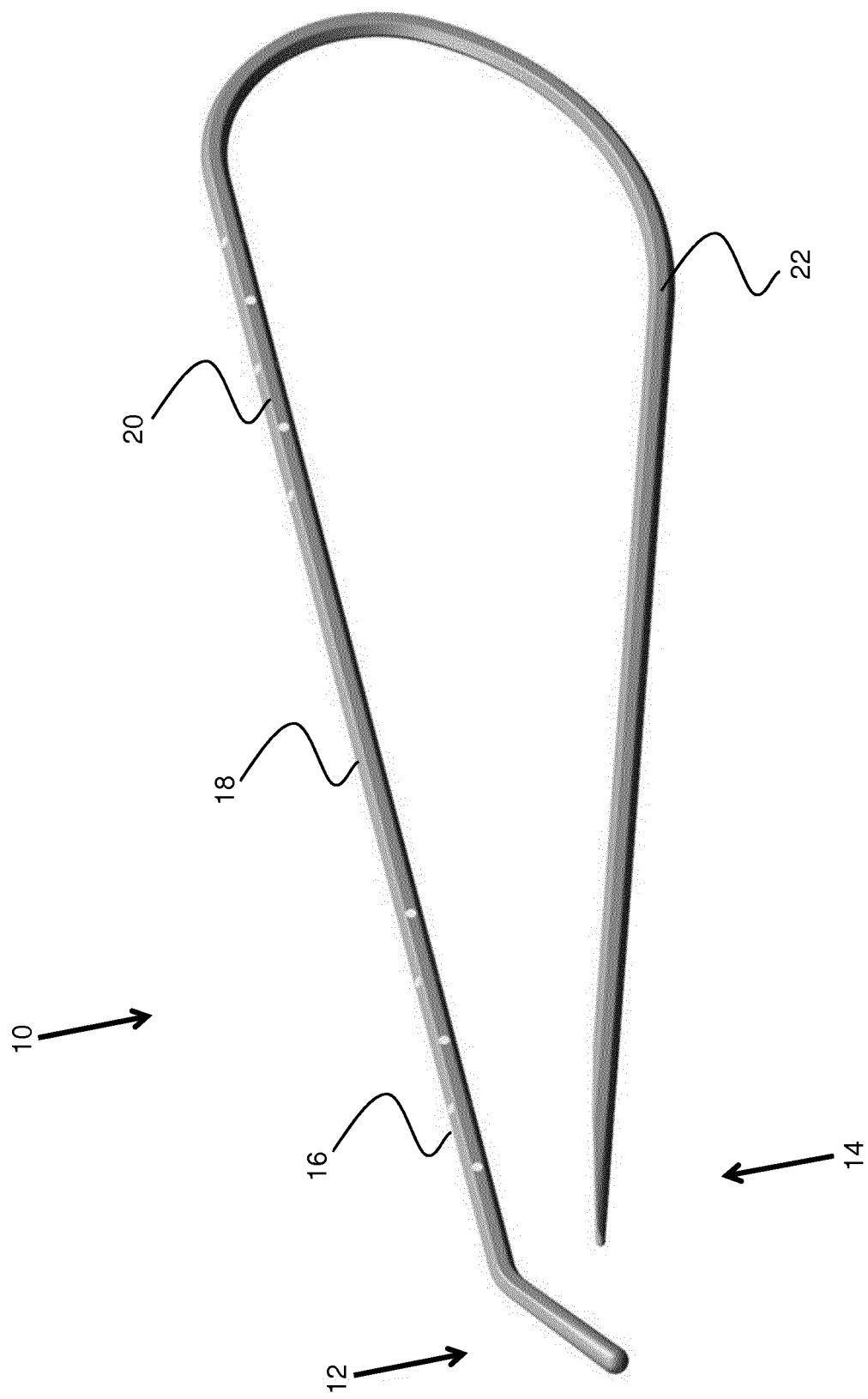
FIG. 1 is a perspective view of a first embodiment of an intubation aid according to the present invention, including shading.
Figure 2:
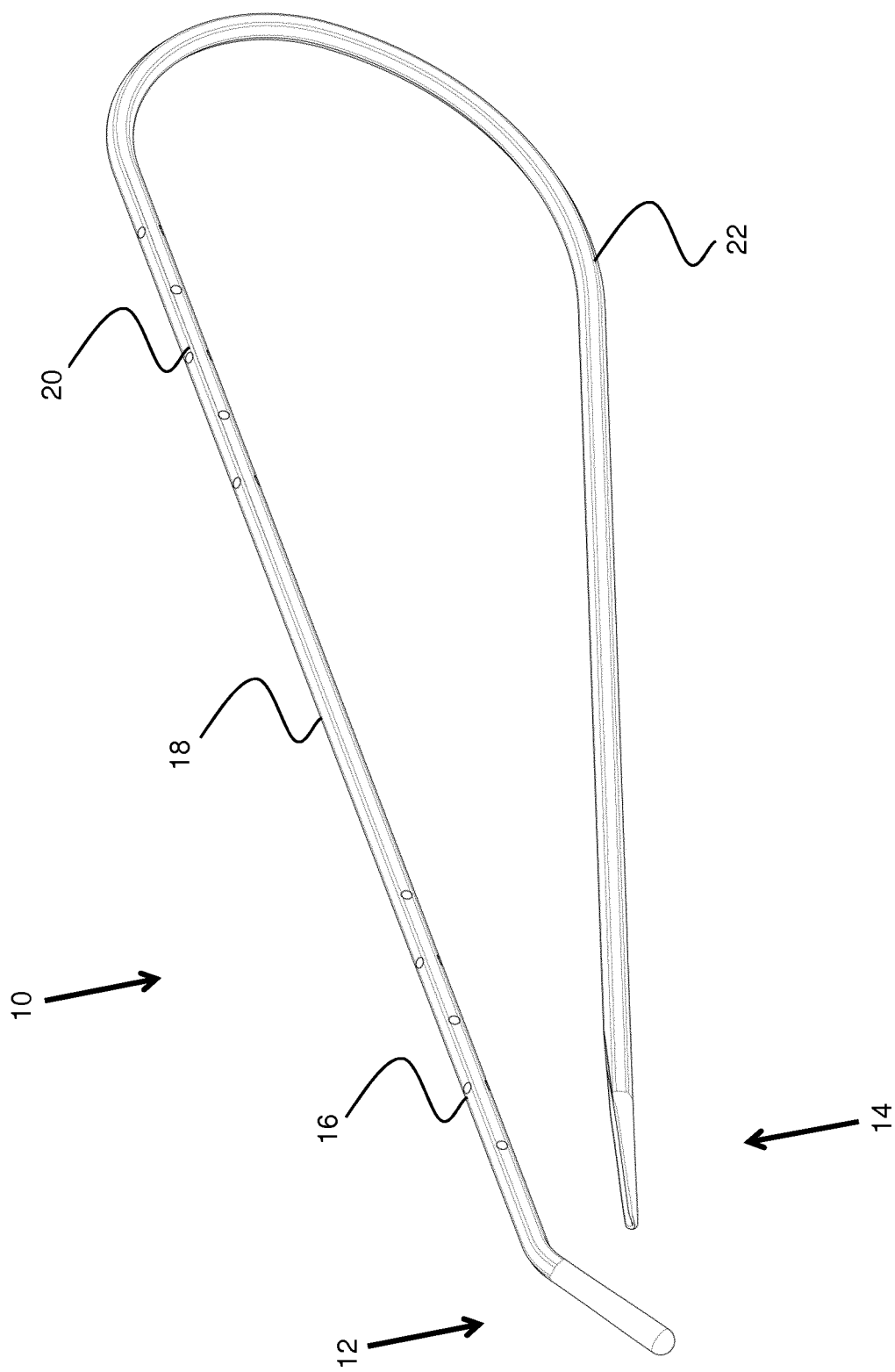
FIG. 2 is a black and white line drawing version of FIG. 1.

An intubation aid according to a first embodiment of the present invention, generally designated 10, is shown in FIGS. 1 to 6. The intubation aid 10 comprises a distal end 12, a proximal end 14, and first 16, second 18, third 20, and fourth 22 intermediate portions. The intubation aid 10 is integrally formed, such that each of the distal end 12, proximal end 14, and first 16, second 18, third 20, and fourth 22 intermediate portions, form a unitary body.

Figure 3A:
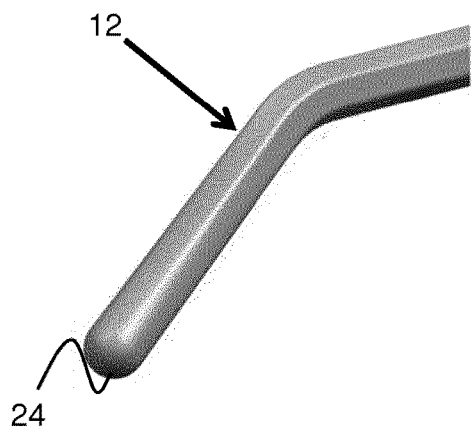
FIG. 3(a) is an enlarged perspective view of a distal end of the intubation aid of FIG. 1 including shading.
Figure 3B:
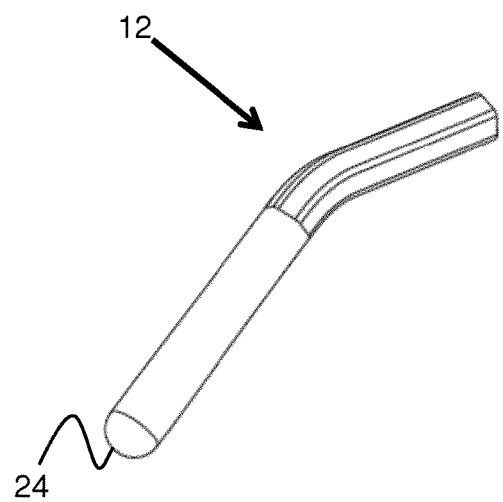
FIG. 3(b) is black and white line drawing version of FIG. 3(a)

The distal end 12, shown in an enlarged view in FIGS. 3(a) and (b), comprises a rounded tip 24, the rounded tip 24 having a circular cross-section. The distal end 12 is flexible, such that the distal end 12 regains its shape when not subjected to an external force.

Figure 4A:
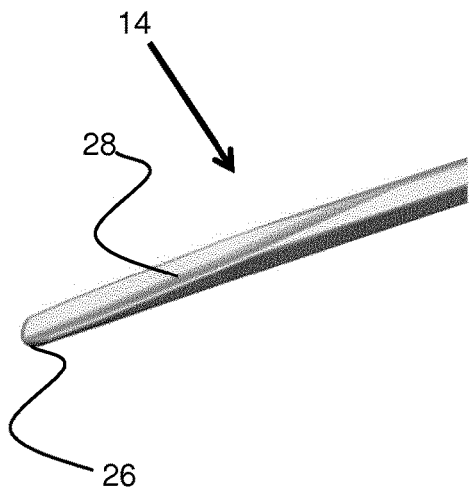
FIG. 4(a) is an enlarged perspective view of a proximal end of the intubation aid of FIG. 1 including shading.
Figure 4B:
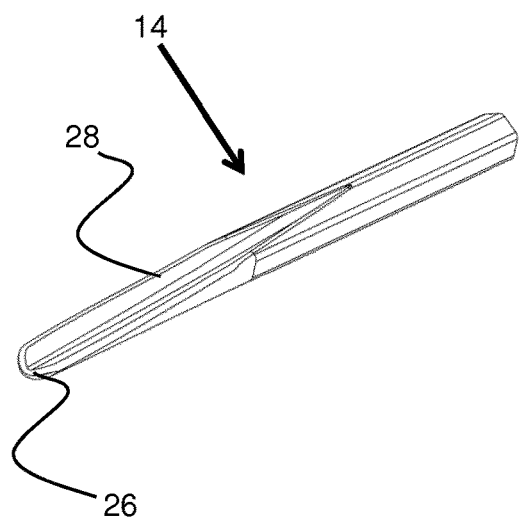
FIG. 4(b) is black and white line drawing version of FIG. 4(a)

The proximal end 14, shown in an enlarged view in FIGS. 4(a) and (b), is tapered toward a proximal tip 26, and comprises a recessed region 28. The recessed region 28 is substantially triangular in form, such that the recessed region 28 is locatable flush against any of the first 16, second 18, third 20, or fourth 22 intermediate portions, which have a hexagonal cross-section, as will be discussed in further detail below. The proximal end 14 is flexible, such that the proximal end 14 regains its shape when not subjected to an external force.

Each of the first 16 and third 20 intermediate portions has a hexagonal cross-section, and is malleable such that the first 16 and third 20 intermediate portions retain their shape when not subjected to an external force. However, the first 16 and third 20 intermediate portions are sufficiently flexible to deform, eg lose their retained shape, as the intubation aid 10 is removed from a patient.

Each of the second 18 and fourth 22 intermediate portions has a hexagonal cross-section, and is flexible such that the first 16 and third 20 intermediate portions regain their shape when not subjected to an external force.

The intubation aid 10 is capable of use either as a bougie, or as a stylet.

Figure 5:
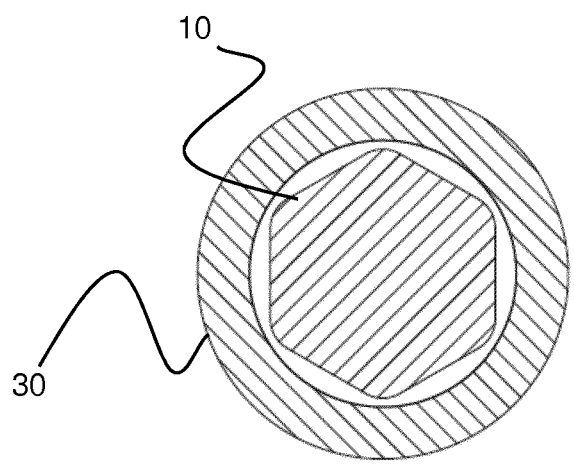
FIG. 5 is a cross-sectional view of the intubation aid of FIG. 1 located within an endotracheal tube.

In a first mode of use, for example use as a conventional bougie, the first 16 and third 20 intermediate portions can optionally be pre-formed into a desired shape before insertion of the intubation aid 10 into the trachea of a patient. Once the intubation aid 10 has been inserted into the trachea, an endotracheal tube can be railroaded over the intubation aid 10 from the proximal end 14 toward the distal end 12. The hexagonal cross-section of the first 16, second 18, third 20, and fourth 22 intermediate portions means that only the edges, and not the faces, of the first 16, second 18, third 20, and fourth 22 intermediate portions, are in contact with the interior surface of the endotracheal tube as it is advanced over the intubation aid 10. The same is true during removal of the intubation aid 10 from the endotracheal tube. A cross-sectional view of the intubation aid 10 located within an endotracheal tube 30 is shown in FIG. 5.

The intubation aid 10 according to the present invention may thus have a lower cross-sectional area in contact with the interior surface of the endotracheal tube 30 than intubation aids previously known in the art. This may thus reduce friction and increase the ease of insertion of an endotracheal tube 30, which is of particular importance during medical emergencies. Furthermore, the intubation aid may remove or lessen the need for lubrication of the interior of an endotracheal tube 30 prior to insertion.

When the endotracheal tube 30 is in position over the intubation aid 10, the intubation aid 10 may be withdrawn, with the cross-section of the first 16, second 18, third 20, and fourth 22 intermediate portions again reducing friction and ease of removal from the endotracheal tube 30.

In a second mode of use, for example use as a conventional stylet, an endotracheal tube may be railroaded over the intubation aid 10 in a similar manner to that discussed above, although this time prior to insertion. The first 16 and third 20 intermediate portions can be pre-formed into a desired shape, thus pre-forming the endotracheal tube to a desired shape, before insertion of the intubation aid 10 and endotracheal tube into the trachea of a patient.

Figure 6:
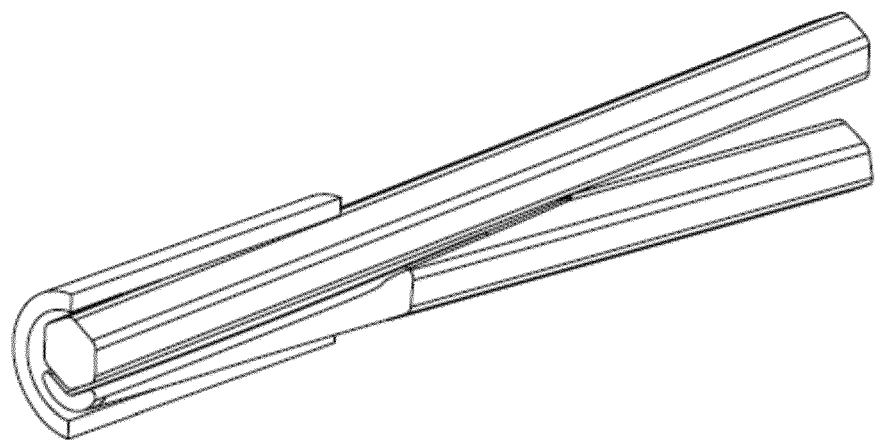
FIG. 6 is a cut-away view of a proximal end of the intubation aid of FIG. 1 in cooperation with the main body of the intubation aid, whilst located within a proximal end of an endotracheal tube.
Figure 7:
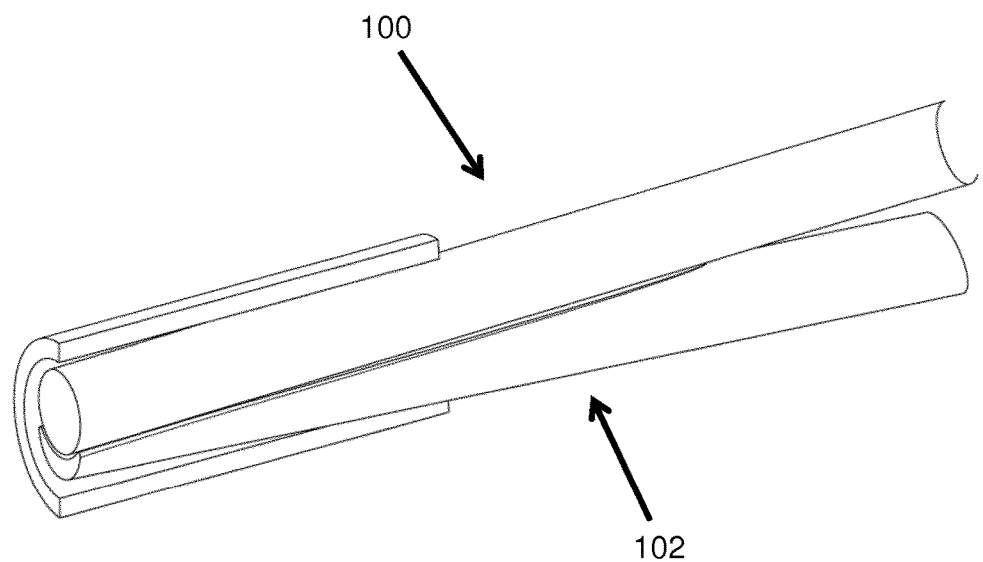
FIG. 7 is a cut-away view of a proximal end of an alternative embodiment of an intubation aid of the present invention in cooperation with the main body of the intubation aid, whilst located within a proximal end of an endotracheal tube.

When the endotracheal tube 30 is in position over the intubation aid 10, the proximal end 14 of the intubation aid 10 can be wedged into a proximal end of the endotracheal tube 30 such that the recessed region 28 accommodates a portion of one of the first 16, second 18, third 20, or fourth 22 intermediate portions. Such a configuration is shown in FIG. 6. The combination of the proximal end 14 and one of the first 16, second 18, third 20, and fourth 22 intermediate portions may be of a width equal to or greater than an internal width of the endotracheal tube 30, such that the endotracheal tube 30 is held in position relative to the intubation aid. Rotation of the intubation aid 10 relative to the endotracheal tube 30 may also be prevented, such that a user knows the alignment of the intubation aid 10, and in particular the rounded tip 24.

Furthermore, such a configuration may cause the intubation aid 10 to form a partial loop, which may be used as a handle by a user to assist insertion of the combined intubation aid 10 and endotracheal tube 30 into the trachea of a patient.

Once the relative positions of the intubation aid 10 and endotracheal tube 30 are fixed, the combined intubation aid 10 and endotracheal tube 30 are inserted into the trachea of a patient.

In a further mode of use, the endotracheal tube 30 is inserted over the intubation aid 10 prior to insertion into a patient's trachea, such that the rounded tip 24 protrudes from a distal end of the endotracheal tube 30, but the proximal end 14 is not wedged into the endotracheal tube 30. Furthermore, the first 16 and third 20 intermediate portions are not pre-formed. In this mode of use, the intubation aid 10 can be rotated within the endotracheal tube 30 to obtain a correct alignment of the rounded tip 24 prior to and/or during insertion. The hexagonal cross-section of the first 16, second 18, third 20 and fourth 22 intermediate portions may increase the ease of rotation of the intubation aid 10 within the endotracheal tube 30.

An alternative embodiment of an intubation aid 100 according to the present invention is shown in FIG. 6. This embodiment of the intubation aid 100 is substantially the same as the first embodiment of the intubation aid 10, and differs only in the form of the proximal end 102. The proximal end 102 of the intubation aid 100 transitions to a circular cross-section, instead of the hexagonal cross-section of the intubation aid 10 of the first embodiment. To correspond with this circular cross-section, the proximal end region of the intubation aid 100 has an arcuate recess for receiving a lower region of the circular cross-section when the proximal end 102 is wedged into an endotracheal tube 30, as shown in FIG. 6.

Although the alternative embodiment 100 may fix the relative positions of the intubation aid 100 and the endotracheal tube 30, a hexagonal cross-section has been found found to have increased fixing capabilities relative to a circular cross-section, and furthermore requires the proximal end 24 of the intubation aid 10 to be inserted into the endotracheal tube 30 with less force.

Figure 8:
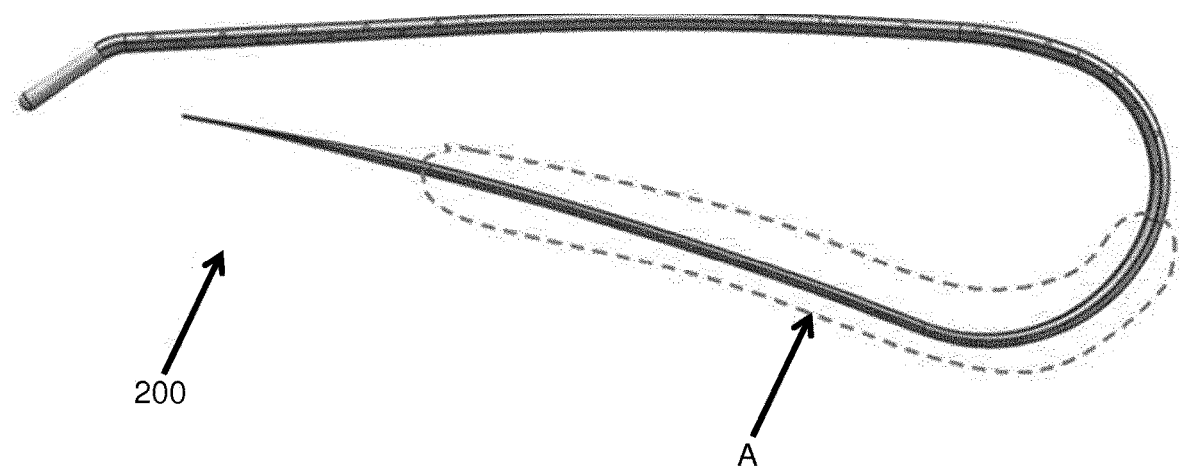
FIG. 8 is a side view of an alternative embodiment of an intubation aid of the present invention.
Figure 9:
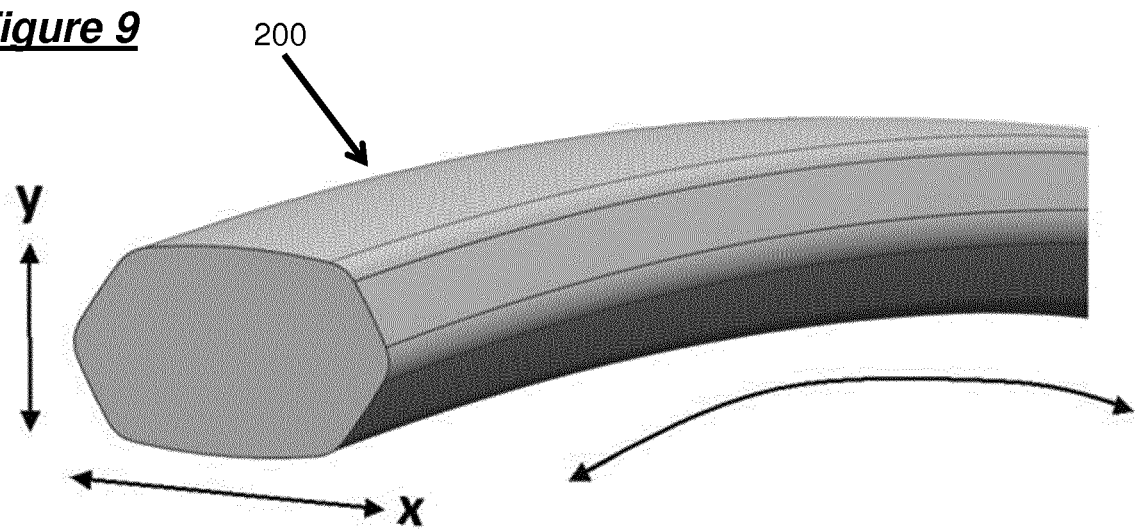
FIG. 9 is an enlarged cross-sectional view of the region labelled A in FIG. 8.

A further alternative embodiment of an intubation aid 200 according to the present invention is shown in FIGS. 8 and 9. The intubation aid 200 is substantially the same as the first embodiment of the intubation aid 10, and differs only in that the intubation aid 200 has a flattened hexagonal cross-section, ie a cross-sectional shape of reduced height, in the region labelled A, as shown in FIG. 9.

This flattened cross-sectional shape has been found particularly beneficial where the proximal end 14 of the intubation aid 200 is be wedged into a proximal end of the endotracheal tube 30, and in particular the flattened cross-sectional shape has been found to prevent kinking of the intubation aid in such a configuration.

The invention claimed is:

1. An intubation aid for insertion into an endotracheal tube, the intubation aid comprising:
    a distal end region;
    a distal intermediate region connected to the distal end region and having a cross-sectional shape having at least one vertex defining a longitudinally extending edge, such that the intubation aid is supported within the endotracheal tube, in use, by the longitudinally extending edge;
    a proximal intermediate region connected to the distal intermediate region and having a flattened cross-sectional shape having orthogonal major and minor axes, wherein the major axis is at least 1.2 times larger than the minor axis; and
    a proximal end region connected to the proximal intermediate region, wherein at least one of:
        the proximal end region of the intubation aid comprises a taper, such that, when the intubation aid is bent, in use, the proximal end region can be wedged into a proximal end of the endotracheal tube at a portion of the distal or proximal intermediate region; and
        the proximal end region of the intubation aid has a cut-out and/or recessed portion, such that, when the intubation aid is bent, in use, the proximal end region of the intubation aid can be wedged into the proximal end of the endotracheal tube with a portion of the distal or proximal intermediate region received within the cut-out and/or recessed portion of the proximal end region.

2. An intubation aid as claimed in claim 1, wherein the longitudinally extending edge is defined across the entire length of distal and proximal intermediate regions of the intubation aid.

3. An intubation aid as claimed in claim 1, wherein the proximal end region of the intubation aid comprises the taper, such that, when the intubation aid is bent, in use, the proximal end region can be wedged into the proximal end of the endotracheal tube at the portion of the distal or proximal intermediate region.

4. An intubation aid as claimed in claim 1, wherein the proximal end region of the intubation aid has the cut-out and/or recessed portion, such that, when the intubation aid is bent, in use, the proximal end region of the intubation aid can be wedged into the proximal end of the endotracheal tube with the portion of the distal or proximal intermediate region received within the cut-out and/or recessed portion of the proximal end region.

5. An intubation aid as claimed in claim 1, wherein:
    the distal intermediate region has a regular polygonal cross-sectional shape; and
    the proximal intermediate region has a flattened polygonal cross-sectional shape.

6. An intubation aid as claimed in claim 1, wherein:
    the distal end region of the intubation aid comprises a rounded tip, the rounded tip comprising a circular cross-section and being integrally formed with the intubation aid;
    when not subjected to an external force, the distal end region is bent at an unflexed angle with respect to the distal intermediate region; and
    the distal end region is sufficiently flexible to be bent at a flexed angle different from the unflexed angle, but regains the unflexed angle when not subjected to an external force.

7. An intubation aid as claimed in claim 1, wherein the proximal end region of the intubation aid comprises a handle having a polygonal cross-section.

8. An intubation aid as claimed in claim 1, wherein at least a portion of the intubation aid is flexible.

9. An intubation aid as claimed in claim 1, wherein at least a portion of the intubation aid is malleable.

10. An intubation aid as claimed in claim 1, wherein the cross-sectional shape of the distal intermediate region comprises at least three vertices.

11. An intubation aid as claimed in claim 1, wherein the cross-sectional shape of the distal intermediate region comprises six vertices.

12. An intubation aid as claimed in claim 1, wherein the intubation aid comprises a unitary body.

13. An intubation aid as claimed in claim 1, wherein the intubation aid configured to be selectively used as either a bougie or a stylet.

14. Apparatus comprising an endotracheal tube and an intubation aid according to claim 1.

15. An intubation aid as claimed in claim 1, wherein:
    the distal intermediate region has a regular hexagonal cross-sectional shape having six vertices defining six longitudinally extending edges; and
    the proximal intermediate region has a flattened hexagonal cross-sectional shape having two opposing, relatively wide sides and four relatively narrow sides, wherein the minor axis bisects the two relatively wide sides.

16. An intubation aid as claimed in claim 1, wherein the distal intermediate region comprises:
   a first distal intermediate sub-region connected to the distal end region;
   a second distal intermediate sub-region connected to the first distal intermediate sub-region; and
   a third distal intermediate sub-region connected to the second distal intermediate sub-region, wherein:
     the first and third distal intermediate sub-regions are sufficiently malleable to retain a bent shape when not subjected to an external force; and
     the second distal intermediate sub-region and the proximal intermediate region are sufficiently flexible to be bent, but regain a straight shape when not subjected to an external force.

17. An intubation aid as claimed in claim 16, wherein:
   the distal end region of the intubation aid comprises a rounded tip, the rounded tip comprising a circular cross-section and being integrally formed with the intubation aid;
   when not subjected to an external force, the distal end region is bent at an unflexed angle with respect to the distal intermediate region;
   the distal end region is sufficiently flexible to be bent at a flexed angle different from the unflexed angle, but regains the unflexed angle when not subjected to an external force;
   the distal intermediate region has a regular hexagonal cross-sectional shape having six vertices defining six longitudinally extending edges;
   the proximal intermediate region has a flattened hexagonal cross-sectional shape having two opposing, relatively wide sides and four relatively narrow sides, wherein the minor axis bisects the two relatively wide sides;
   the longitudinally extending edge is defined across the entire length of distal and proximate intermediate regions of the intubation aid; and
   the intubation aid is configured to be selectively used as either a bougie or a stylet.

18. Apparatus comprising an endotracheal tube and an intubation aid according to claim 17.

\* \* \* \* \*